US007713283B2

(12) United States Patent
Forsberg

(10) Patent No.: US 7,713,283 B2
(45) Date of Patent: May 11, 2010

(54) TISSUE PUNCTURE CLOSURE DEVICE WITH MAGAZINE FED TAMPING SYSTEM

(75) Inventor: Andrew Thomas Forsberg, Minneapolis, MN (US)

(73) Assignee: St. Jude Medical Puerto Rico, LLC, Caguas, PR (US)

( * ) Notice: Subject to any disclaimer, the term of this patent is extended or adjusted under 35 U.S.C. 154(b) by 1381 days.

(21) Appl. No.: 11/103,257

(22) Filed: Apr. 11, 2005

(65) Prior Publication Data

US 2006/0229673 A1  Oct. 12, 2006

(51) Int. Cl.
A61B 17/08 (2006.01)
A61D 1/00 (2006.01)

(52) U.S. Cl. ...................................... 606/213
(58) Field of Classification Search ............... 606/213, 606/232

See application file for complete search history.

(56) References Cited

U.S. PATENT DOCUMENTS

| 4,744,364 | A |   | 5/1988 | Kensey |
|---|---|---|---|---|
| 5,021,059 | A | * | 6/1991 | Kensey et al. ............. 606/213 |
| 5,222,974 | A |   | 6/1993 | Kensey et al. |
| 5,282,827 | A |   | 2/1994 | Kensey et al. |
| 5,290,310 | A |   | 3/1994 | Makower et al. |
| 5,324,306 | A |   | 6/1994 | Makower et al. |
| 5,411,520 | A |   | 5/1995 | Nash et al. |
| 5,431,666 | A |   | 7/1995 | Sauer et al. |
| 5,507,744 | A |   | 4/1996 | Tay et al. |
| 5,527,322 | A |   | 6/1996 | Klein et al. |
| 5,531,759 | A | * | 7/1996 | Kensey et al. ............. 606/213 |
| 5,540,705 | A | * | 7/1996 | Meade et al. ............. 606/145 |
| 5,728,114 | A |   | 3/1998 | Evans et al. |
| 5,792,152 | A |   | 8/1998 | Klein et al. |
| 5,810,810 | A |   | 9/1998 | Tay |
| 5,860,991 | A |   | 1/1999 | Klein et al. |
| 6,063,085 | A |   | 5/2000 | Tay et al. |
| 6,206,893 | B1 |   | 3/2001 | Klein et al. |
| 6,425,911 | B1 |   | 7/2002 | Akerfeldt et al. |
| 6,508,828 | B1 |   | 1/2003 | Akerfeldt et al. |
| 6,860,895 | B1 |   | 3/2005 | Akerfeldt et al. |

OTHER PUBLICATIONS

International Search Report and Written Opinion from corresponding International Application No. PCT/US06/13223, dated Aug. 8, 2007 (7 pages).

* cited by examiner

*Primary Examiner*—(Jackie) Tan-Uyen T. Ho
*Assistant Examiner*—Melanie Tyson
(74) *Attorney, Agent, or Firm*—Holland & Hart

(57) ABSTRACT

The present invention is directed to methods and apparatus for sealing a puncture or incision formed percutaneously in tissue separating two internal portions of the body of a living being with an anchor, a sealing plug and a filament connecting the anchor and sealing plug. The method and apparatus provide a magazine fed tamping system for automatic tamping and/or cinching of the sealing plug when the apparatus is withdrawn from the puncture site. The automatic tamping and/or cinching is facilitated by transducing a motive force generated by the withdrawal of the apparatus into a tamping and/or cinching force.

15 Claims, 7 Drawing Sheets

TISSUE PUNCTURE CLOSURE DEVICE WITH MAGAZINE FED TAMPING SYSTEM

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963; 6,090,130; and 6,045,569 and related patents that are hereby incorporated by reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be retracted from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present invention meets the above-described needs and others. Specifically, the present invention provides methods and systems for closing internal tissue punctures. However, unlike prior systems, the present invention provides automatic tamping to a sealing plug as the closure device is retracted. In addition, the present invention allows the automatic tamping system to receive a plurality of tamping devices arranged in a magazine that cooperate to form a longer tamping device.

In one of many possible embodiments, the present invention provides an internal tissue puncture closure device. The device comprises a filament extending from a first end of the closure device to a second end of the closure device, an anchor for insertion through the tissue wall puncture attached to the filament at the second end of the closure device, a sealing plug slidingly attached to the filament adjacent to the anchor, and a driving mechanism for tamping the sealing plug toward the second end. The driving mechanism comprises a magazine housing a plurality of separate tamping devices. The plurality of separate tamping devices may each comprise a rack. The magazine may include a biasing member, and the plurality of separate tamping devices may be stacked in the magazine and biased in a first direction by the biasing member. The driving mechanism also comprises a transducer capable of effecting a distal force on one or more of the plurality of separate tamping devices upon withdrawal of at least a portion of the closure device from a tissue puncture. The transducer may comprise a first gear and spool assembly with a portion of the filament wound on the spool, such that one or more of the plurality of tamping devices is directly or indirectly driven by the first gear. The first gear and spool assembly may be disposed on a common axis and interconnected, and the transducer may include a second gear meshed with the first gear. One or more of the plurality of tamping devices may be directly driven linearly by the second gear. A third gear may also be meshed with the first gear. Accordingly, one or more of the plurality of tamping devices may be directly driven linearly by the second and third gears. One or more of the plurality of tamping devices may abut and drive a tamping tube and the sealing plug toward the anchor.

According to some embodiments, the transducer includes a first gear and spool assembly with a portion of the filament wound upon the spool, the first gear and spool assembly disposed on a common axis and interconnected, a magazine feed gear meshed with the first gear, and a tamper gear meshed with the first gear, where one or more of the plurality of tamping devices is fed by the magazine feed gear to the tamper gear and driven by the tamper gear to tamp the sealing plug toward the anchor.

According to some aspects of the invention, the driving mechanism comprises an automatic driving mechanism. The plurality of tamping devices may be driven by the automatic driving mechanism in response to retraction of the closure device, and a tamping tube is driven by the plurality of tamping devices to tamp the sealing plug. The driving mechanism may comprise a transducer for effecting a tamping force on the sealing plug upon withdrawal of the closure device from the tissue wall puncture. As mentioned above, the transducer may include a first gear and spool assembly with a portion of the filament wound thereon, and one or more of the plurality of tamping devices may be directly or indirectly driven by the first gear. The spool may rotate and drive the first gear in a first direction, and the first gear may drive one or more of the plurality of tamping devices in a second direction, when the anchor is deployed and the closure device is retracted from the tissue wall puncture.

Another aspect of the invention provides a tissue puncture closure device for partial insertion into and sealing of a tissue puncture in an internal tissue wall accessible through a percutaneous incision. The device comprises a handle portion, a carrier tube extending from the handle portion, a filament extending from the handle portion and through the carrier tube, a sealing plug disposed on the filament, a gear train housed in the handle portion, a spool operatively connected to the gear train with a portion of the filament wound on the spool, and a magazine fed tamping device operatively connected to the gear train. The magazine fed tamping device may comprise a spring loaded set of stacked racks engageable with the gear train. The gear train may comprise a master gear, and two slave gears each meshed with the master gear. The apparatus may further comprise an anchor attached to the filament at a distal end of the carrier tube, where the filament unwinds from the spool and drives the gear train in response to retraction of the handle portion from the tissue puncture if the anchor is deployed therein. The gear train may automatically drive the magazine fed tamping device, and the magazine fed tamping device tamps the sealing plug toward the anchor.

Another aspect of the invention provides a method of sealing a tissue puncture in an internal tissue wall accessible through a percutaneous incision. The method comprises withdrawing a closure device from the tissue puncture, feeding a tamping device stack to a tranducer, and automatically transducing a motive force generated by withdrawal of the closure device in a first direction to a tamping force on the tamping device stack in a second direction. The feeding may further comprise biasing the tamping device stack with a spring in a magazine housing the tamping device stack. The method may further comprise applying the tamping force in the second direction to a sealing plug. The method may further comprise transferring the motive force to one or more tamping devices of the tamping device stack, the one or more tamping devices comprising a rack slidingly disposed about a filament, the filament being connected to the sealing plug. The transferring may further comprise automatically unwinding the filament from a spool by deploying an anchor attached to the filament inside the tissue puncture, and withdrawing the closure device from the tissue puncture. The transferring may include driving a gear train meshed with the rack and the spool via the unwinding.

According to some embodiments, each tamping device of the tamping device stack comprises a rack. The automatically transducing may then comprise rotating a first gear meshed with a magazine feed gear, where the feeding comprises meshing a first tamping device of the tamping device stack with the magazine feed gear, moving the first tamping device linearly away from the magazine feed gear, urging a second tamping device of the tamping device stack laterally toward the magazine feed gear, meshing the second tamping device with the magazine feed gear, and moving the first and second tamping devices linearly away from the magazine feed gear. The automatically transducing may also comprise rotating a first gear meshed with a magazine feed gear, meshing a first tamping device of the tamping device stack with the magazine feed gear, moving the first tamping device linearly away from the magazine feed gear, meshing the first tamping device with a tamper gear, urging a second tamping device of the tamping device stack laterally toward the magazine feed gear, meshing the second tamping device with the magazine feed gear, and moving the first tamping device linearly away from the tamper gear and the second tamping device linearly away from the feed gear.

Another aspect of the invention provides a method of sealing a tissue puncture in an internal tissue wall accessible through a percutaneous incision. The method comprises providing a tissue puncture closure device comprising a filament connected at its distal end to an anchor and to a sealing plug located proximal of the anchor for disposition and anchoring about the tissue puncture, the tissue puncture closure device also comprising an automatic magazine fed tamping device, inserting the tissue puncture closure device into the percutaneous incision, deploying the anchor into the tissue puncture, at least partially withdrawing the closure device from the percutaneous incision, automatically tamping the sealing plug toward the anchor upon withdrawal of the closure device from the internal tissue wall puncture with the automatic magazine fed tamping device, cutting the filament, and leaving the anchor and the sealing plug at the tissue puncture. The automatically tamping may comprise biasing a stack of racks toward a magazine feed gear, unwinding the filament from a spool to rotate the spool, driving a first gear with the spool, driving the magazine feed gear with the first gear, and driving two or more racks of the stack toward the sealing plug.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
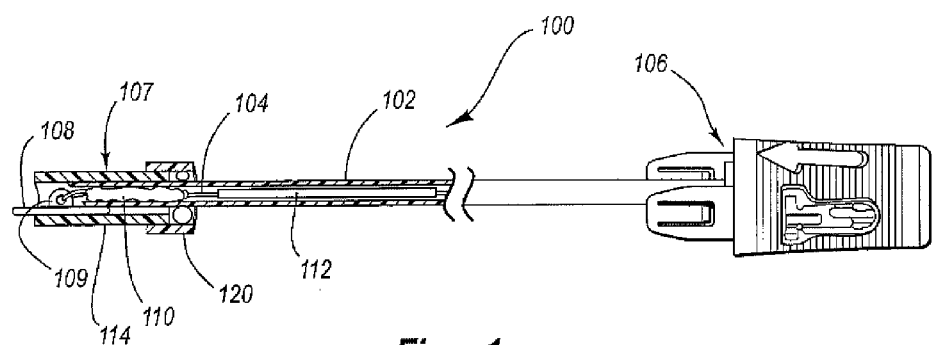
FIG. 1 is a partial cut-away view of a tissue closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is not properly seated against an exterior situs of the arteriotomy. If the plug does not seat against the arteriotomy, there is a potential for elongated bleeding. The present invention describes methods and apparatus to reduce or eliminate movement or misplacement of the sealing plug. While the vascular instruments shown and described below include insertion sheaths and puncture sealing devices, the application of principles described herein are not limited to the specific devices shown. The principles described herein may be used with any vascular closure device. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps, but not by excessive force. "Engage" and "engageable" are also used broadly to mean interlock, mesh, or contact between two devices. A "spool" is a cylinder or other device on which something else is at least partially wound. A "magazine" is any compartment attached to or feeding a machine, used for storing or supplying necessary material. A "rack" is a toothed or tined bar capable of meshing with a gear, wheel, pinion, or other toothed machine part. A "gear train" is a series of two or more engaged gears. "Urge" or "urging" is used broadly and means to force or drive forward or onward. A "lumen" refers to any open space or cavity in a bodily organ, especially in a blood vessel. The term "effecting" means producing an outcome, achieving a result, or bringing about. A "transducer" is a device capable of converting a force or other input energy in one form into output energy or forces of another form or direction. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
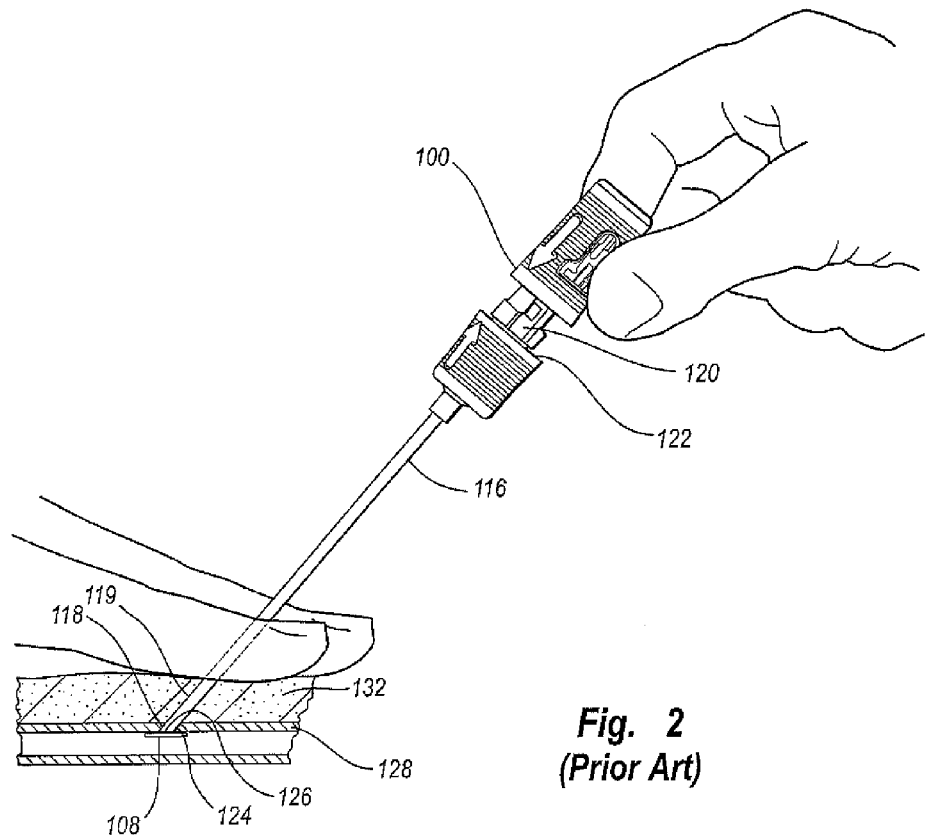
FIG. 2 is a side view of the tissue closure device of FIG. 1 engaged with an artery according to the prior art.
Figure 3:
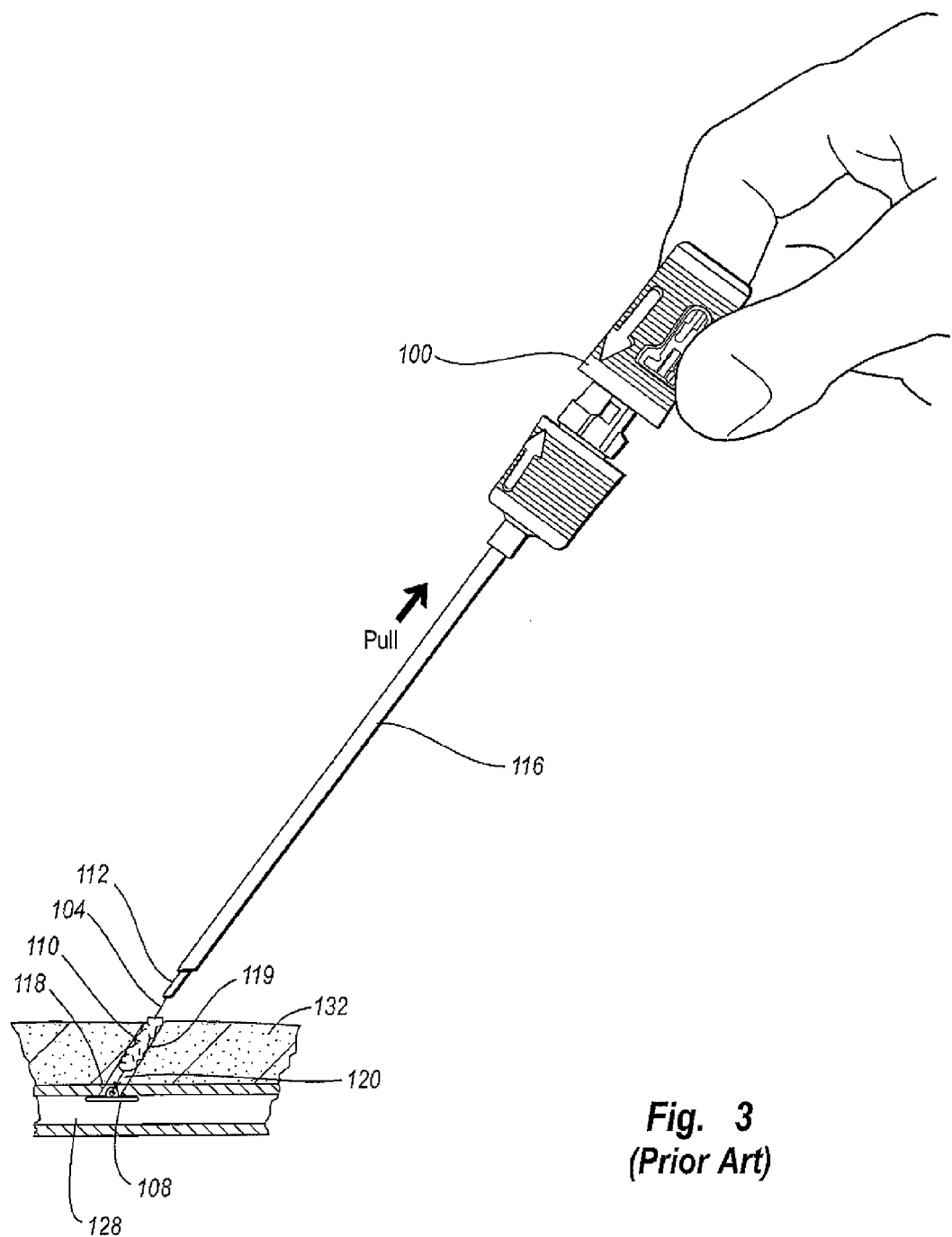
FIG. 3 is a side view of the tissue closure device of FIG. 1 being withdrawn from an artery according to the prior art to deploy a collagen sponge.
Figure 4:
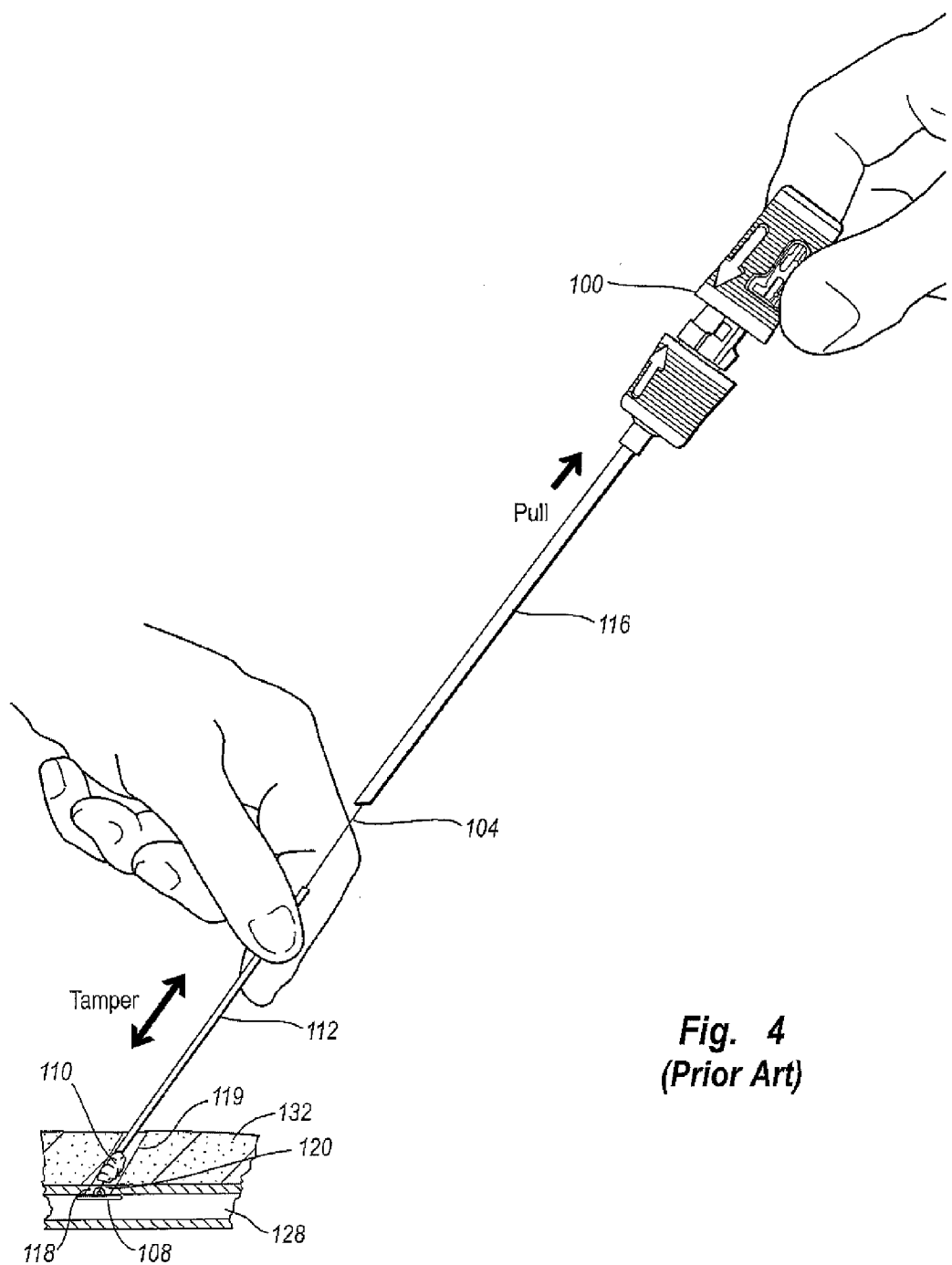
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, depositing the collagen pad 110 in the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, the tamping of the collagen pad 110 cannot commence until the sheath 116 has been removed so as to expose the tamping tube 112 for manual grasping. Under certain conditions, removal of the sheath 116 prior to tamping the collagen pad 110 causes the collagen pad 110 to retract from the tissue puncture 118, creating a gap 120 between the collagen pad 110 and the puncture 118. The gap 120 may remain even after tamping as shown in FIG. 4, and sometimes results in only a partial seal and bleeding from the tissue puncture 118.

Therefore, the present specification describes a tissue puncture closure device that drives a sealing plug toward a tissue puncture upon withdrawal of the tissue puncture closure device from the tissue puncture site. The mechanism for driving the sealing plug is preferably automatic and comprises a magazine housing a plurality of separate tamping devices. While the preferred embodiments of the tissue puncture closure device are shown and described below, the principles of the present specification may be incorporated into any of a number of tissue closure devices. The specific embodiments described below are for illustrative purposes only, and are not limiting.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
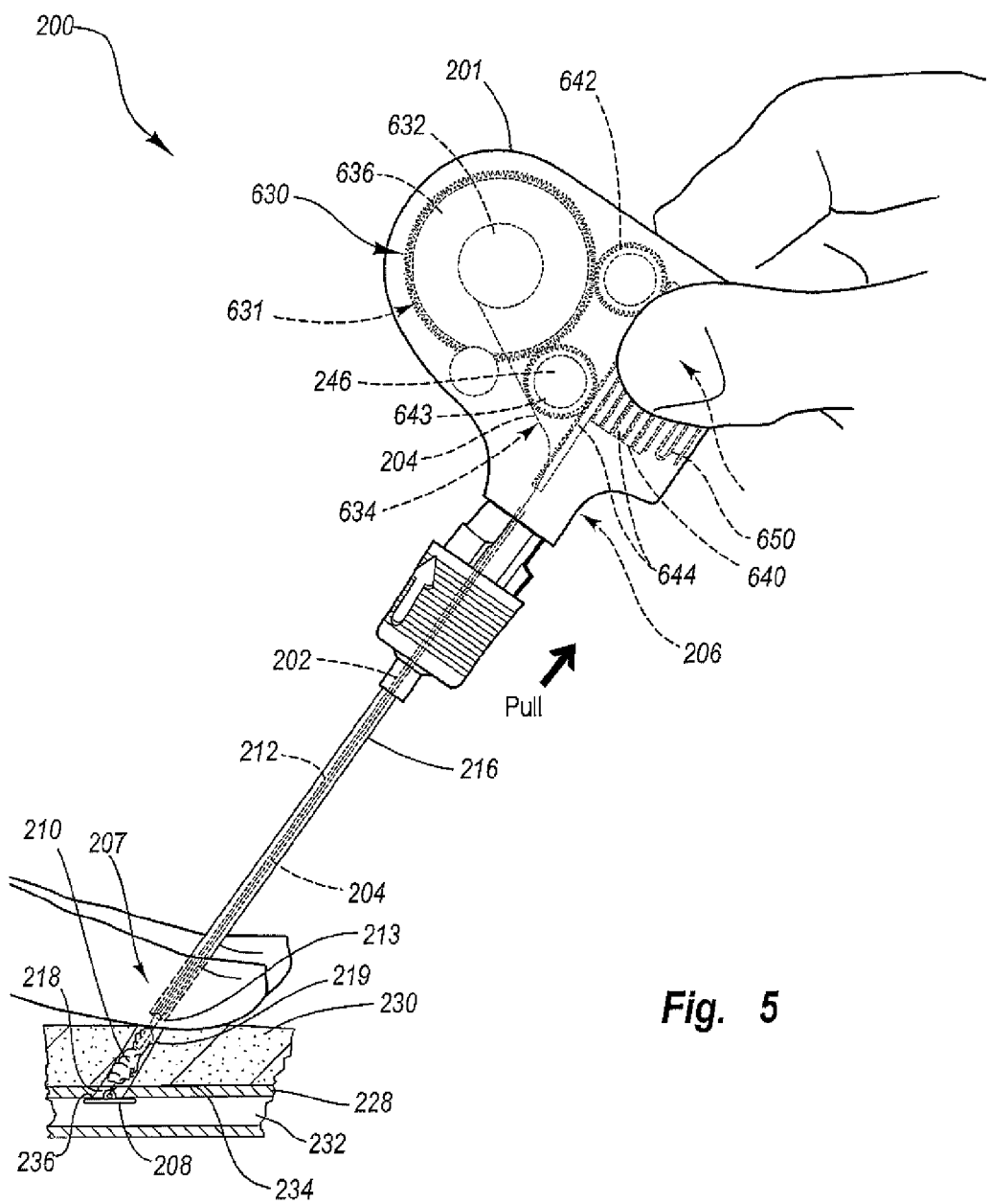
FIG. 5 is a side view of a tissue closure device with a tamping or driving mechanism having a magazine fed tamping system, the closure device shown engaged with an artery according to one embodiment of the present invention.

Referring now to FIG. 5, a closure apparatus, for example an internal tissue puncture closure device 200, is shown according to one embodiment of the present invention. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of blood vessel (e.g., arterial) punctures. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the internal tissue closure device 200 of the present invention.

The internal tissue closure device 200 includes a handle portion 201 at a first or proximal end 206 and a second or distal end 207. A carrier tube 202 extends from the handle portion 201 to the distal end 207. The carrier tube 202 may be made of plastic or other material and is designed for insertion through a sheath 216, which is designed for insertion through a percutaneous incision 219 in a tissue layer 230 and into a lumen 232. According to FIG. 5, the lumen 232 comprises an interior portion of a femoral artery 228.

At the distal end 207 of the carrier tube 202 there is an anchor 208 and a sealing plug 210. The anchor 208 of the present embodiment is an elongated, stiff, low-profile member arranged to be seated inside the artery 228 against an artery wall 234 contiguous with a puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

The sealing plug 210 and anchor 208 are connected to one another by a filament or suture 204 that is also biologically resorbable. The anchor 208, the sealing plug 210, and the suture 204 are collectively referred to as the "closure elements" below. As shown in FIG. 5, the anchor 208 is arranged adjacent to and exterior of the distal end 207 of the sheath 216, while the sealing plug 210 is initially disposed within carrier tube 202. Although the anchor 208 is shown deployed with a first surface 236 abutting the artery wall 234, it will be understood that initially the anchor is arranged axially along the carrier tube 202 to facilitate insertion into the lumen 232 (see, for example, the anchor 108 of FIG. 1). The suture 204 extends distally from the first end 206 of the handle portion 201 and through the carrier tube 202 to the second end 207. The suture 204 may be threaded through one or more perforations in the sealing plug 210, through a hole in the anchor 208, and proximally back toward the carrier tube 202 to the sealing plug 210. Accordingly, the sealing plug 210 is disposed on or slidingly attached to the suture 204 at the second end 207 of the tissue puncture closure device 200.

The suture 204 is preferably threaded again through a perforation or series of perforations in the sealing plug 210. The suture 204 may also be threaded around itself to form a self-tightening slip-knot. The suture 204 thus connects the anchor 208 and the sealing plug 210 in a pulley-like arrangement to cinch the anchor 208 and the sealing plug 210 together when the carrier tube 202 is pulled away from the anchor 208 and the sealing plug 210, sandwiching and locking the anchor and plug together and thereby sealing the tissue puncture 218.

The carrier tube 202 may house a tamping device, such as a tamping tube 212, for advancing the sealing plug 210 along the suture 204 and toward the anchor 208. The tamping tube 212 is shown located within the carrier tube 202 and proximal of the sealing plug 210. The tamping tube 212 is preferably an elongated tubular member that may be rigid or flexible and formed of any suitable material. For example, according to one embodiment, the tamping tube 212 is made of polyurethane. The suture 204 extends through the tamping tube 212 but is not directly connected thereto. Accordingly, the suture 204 and tamping tube 212 are free to slide past one another. According to the embodiment of FIG. 5, as the suture 204 extends proximally past the tamping tube 212 and attaches to a driving mechanism 630 located within the handle portion 201 at the first end 206 of the closure device 200. One embodiment of the driving mechanism 630 is described in detail below with reference to FIG. 6.

The tamping tube 212 is shown aligned axially with one or more of a plurality of separate tamping devices, such as a plurality of racks 644, some of which are shown housed in a magazine 640 of the driving mechanism 630. The racks 644 comprise a magazine fed tamping device and are receptive of gear teeth and discussed in more detail below with reference to FIG. 6. Alternatively, the tamping tube 212 may be omitted and replaced by one or more of the racks 644.

In practice, the carrier tube 202 of the closure device 200 (containing the closure elements described above) is inserted into the insertion sheath 216, which is shown already inserted within the artery 228. Procedures for placing the insertion sheath 216 within the artery 228 are well known to those of skill in the art having the benefit of this disclosure. As the closure device 200 and the associated closure elements are inserted into the insertion sheath 216, the anchor 208 passes through and out of the distal end of the insertion sheath 216. The anchor 208 is then inserted into the artery lumen 232. As mentioned above, the anchor 208 is initially arranged substantially parallel with the carrier tube 202 to facilitate insertion of the anchor 208 through the percutaneous incision 219 and into the lumen 232.

Following deployment of the anchor 208 within the lumen 232, the closure device 200 is retracted or withdrawn from the insertion sheath 216, which may cause the anchor 208 to catch a monofold at the distal end of the insertion sheath 216 and rotate to the position shown in FIG. 5. However, according to some embodiments, the anchor 208 naturally rotates to the deployed position shown. When resistance to further retraction of the closure device 200 is sensed tactilely by an operator, the closure device 200 and the insertion sheath 216 are withdrawn together, causing the anchor 208 to hold fast within the artery 228 against the artery wall 234. With the anchor 208 secured within the artery 228 at the puncture site 218, further retraction of the closure device 200 and insertion sheath 216 causes the sealing plug 210 to withdraw from the distal end 207 of the carrier tube 202, thereby depositing the plug 210 within the incision or puncture tract 219 opposite of the anchor 208.

However, unlike previous closure devices that require a separate, manual tamping procedure following the planting of the sealing plug 210, the closure device 200 of the present invention automatically tamps the sealing plug 210. The closure device 200 drives the tamping tube 212 toward the sealing plug 210 automatically upon withdrawal of the closure device 200 from the puncture tract 219, tamping the plug 210 toward the anchor 208. Therefore, the sealing plug 210 is tamped while the carrier tube 202 is still arranged adjacent to the puncture 218 in the femoral artery 228, reducing or eliminating any gaps that may otherwise occur between the sealing plug 210 and the puncture 218 in the femoral artery 228.

In addition, by placing tension on or pulling the suture 204 away from the puncture tract 219, the suture 204 cinches and locks (with a slip knot or the like) together the anchor 208 and the sealing plug 210, sandwiching the artery wall 234 between the anchor 208 and sealing plug 210. The force exerted by the tamping tube 212 and the cinching together of the anchor 208 and sealing plug 210 by the filament 204 also causes the sealing plug 210 to deform radially outward within the puncture tract 219 and function as an anchor on the proximal side of the tissue puncture site 218.

Automatically driving the tamping tube 212 toward the sealing plug 210 and/or cinching the plug and the anchor 208 may be facilitated by any of a number of mechanisms. For example, a transducer such as the driving mechanism 630 shown in FIGS. 5-6 may be disposed in the handle portion 201 of the closure device 200. According to the embodiment of FIG. 6, retraction of the closure device 200 automatically effects tamping of the sealing plug 210 (FIG. 5). A retraction force in a first direction may be automatically transduced to a tamping force in a second direction as described below. The automatic transducing of the retraction force to a tamping force is achieved, according to FIG. 6, by the driving mechanism 630 or other transducer.

Figure 6:
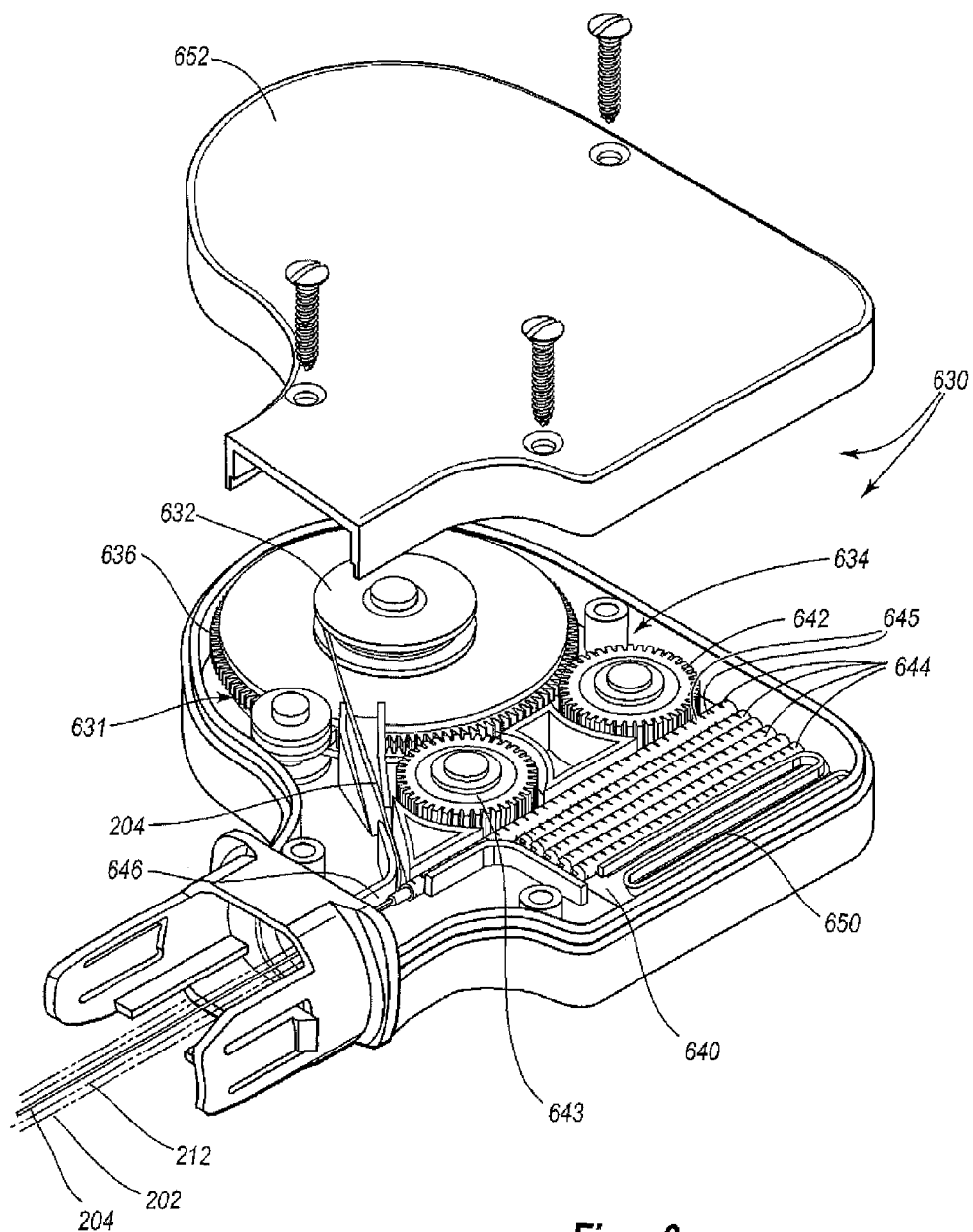
FIG. 6 is a partial perspective view of one embodiment of the driving mechanism and magazine of FIG. 5 according to the present invention.

According to the driving mechanism 630 of FIG. 6, the suture 204 is connected to and/or partially wound about a spool 632 of a first gear and spool assembly 631. The first gear and spool assembly 631 includes both the spool 632 and a first or master gear 636. The spool 632 is operatively connected to the first gear 636 and may be arranged on a common axis as shown in FIG. 6. According to the embodiment of FIG. 6, the first gear 636 is directly connected to the spool 632, although a clutch between the spool and the first gear 636 may be included to limit torque or disengage the spool 632 from the first gear 636. However, both the spool 632 and the first gear 636 tend to rotate at the same angular velocity under normal operating conditions. Withdrawal of the closure device 200 (FIG. 5) from the tissue puncture site (if the anchor 208 (FIG. 5) is deployed) causes the suture 204 to unwind from the spool 632. The spool 632 (and therefore the first gear 636) rotates as the suture 204 unwinds and provides a torsional motive force that may be transduced to a linear tamping force.

Transducing the torsional motive force provided by the spool 632 to the linear tamping force is achieved by a gear train 634 according to the embodiment of FIG. 6. The gear train 634 includes the first gear 636 arranged coaxially with the spool 632 and a second or magazine feed gear 642 meshed with the first gear 636. The gear train 634 may also include a third or tamper gear 643 also meshed with the first gear 636. The first gear 636 drives the second and third gears 642, 643.

According to the embodiment shown in FIG. 6, the suture 204 is wrapped around the spool 632 in a counter-clockwise manner. Therefore, unwinding the suture from the spool causes the first gear 636 to rotate counter-clockwise. The second and third gears 642, 643 thus rotate clockwise. However, according to some embodiments, one or both of the second and third gears 642, 643 may be omitted, and the suture may be wound on the spool 632 either clockwise or counter-clockwise, depending on the desired direction of first gear 636 rotation.

Figure 6A:
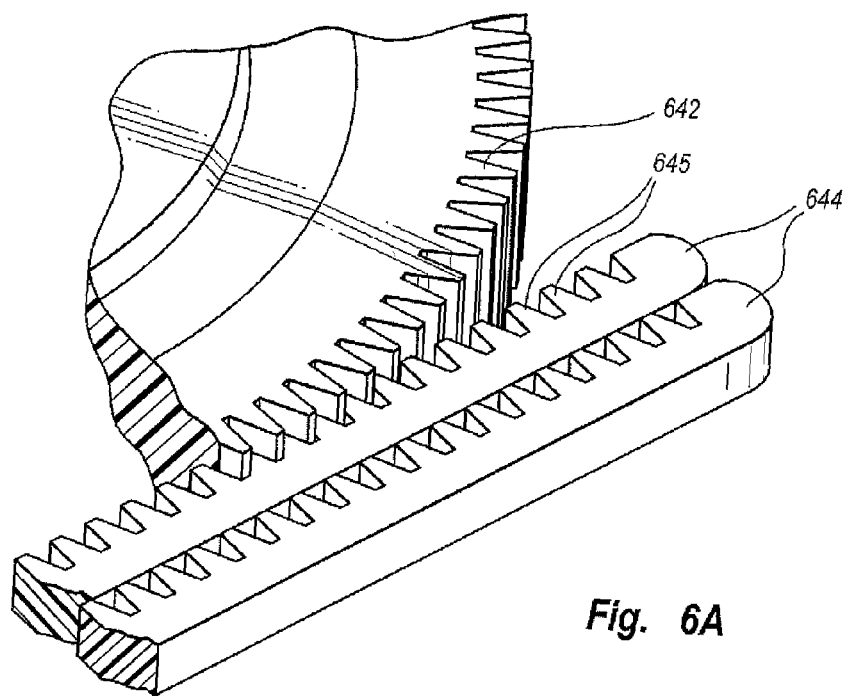
FIG. 6A is a close up view of a portion of FIG. 6.

The magazine fed tamping device comprising the plurality of separate racks 644, is disposed adjacent to the second gear 643. Each of the plurality of separate racks 644 is preferably the same size and shape as shown in FIG. 6 and arranged to be fed individually to the gear train 634 for substantially linear alignment. Several of the racks 644 are shown stacked in the magazine 640. The racks 644 preferably include tines 645 (FIGS. 6, 6A and 7A) which mesh with teeth of the second and third gears 642, 643. A track 646 may guide the racks 644 as they move out of the magazine 640 and distally toward the sealing plug 210 (FIG. 5).

When the spool 632 rotates, the racks 644 are fed by the magazine 640, first to the second gear 642, and then to the third gear 643. As they move out of the magazine 640, the racks 644 are progressively arranged longitudinally and moved distally, abutting and driving the tamping tube 212 (FIG. 5), which in turn drives the sealing plug 210 (FIG. 5). Alternatively, the racks 644 may act as a tamping tube itself and therefore become the "tamping tube 212."

The racks 644 are preferably semi-tubular and partially able to be disposed about the suture 204 longitudinally. The semi-tubular shape of the racks 644 may have a generally U or V-shaped cross section, and provide an open channel or trough 648 through which the suture 204 may enter and exit. The open channel 648 permits the suture 204 and the rack 644 to merge as the spool 632 winds or unwinds. The suture 204 and the rack 644 are not fixedly connected to one another, allowing each to slide freely past the other. Accordingly, with the anchor 208 (FIG. 5) deployed, as the closure device 200 (FIG. 5) is retracted in a first direction, the suture 204 unwinds from the spool 632, which drives the gear train 634. The gear train 634 drives the racks 644 in a second, opposite direction, and the racks 644 drive the tamping tube 212 (FIG. 5).

As mentioned above, the stack of racks 644 is housed in a magazine 640. The magazine 640 includes a biasing member such as a spring 650 urging the stack of racks 644 in a first direction toward the gear train 634. Therefore, as the gear train 634 rotates, it moves an engaged rack 644 distally toward the sealing plug 210 (FIG. 5). When the engaged rack 644 clears the extents of the magazine 640, another rack 644 is fed to the gear train 634. Adjacent racks 644 line up longitudinally and drive the tamping tube 212 (FIG. 5) or the sealing plug 210 (FIG. 5) directly.

It may be desirable in some cases to increase the linear velocity of the racks 644 relative to the linear velocity at which the closure device 200 (FIG. 5) may be withdrawn. An increased linear velocity for the racks 644 may better assure that the sealing plug 210 (FIG. 5) is forced toward the anchor 208 (FIG. 5) while the closure device 200 (FIG. 5) is being withdrawn in an opposite direction. Therefore, according to some embodiments, the gear train 634 may have an overall gear ratio greater than 1:1. For example, the gear ratio may range between approximately 1.5:1 and 3.0:1 for some embodiments, while the gear ratio is about 2.1:1 in other embodiments.

However, it should be noted that the linear velocity of the racks 644 should not be excessively greater than the linear velocity of withdrawal of the closure device, as excessive speed could potentially force the sealing plug 210 (FIG. 5) through the tissue puncture 218 (FIG. 5) and into the lumen 232 (FIG. 5) of the artery 228 (FIG. 5). Likewise, an insufficient opposing force against the anchor 208 (FIG. 5) could potentially result in the anchor 208 (FIG. 5) being pulled out of place from within the artery 228 (FIG. 5). However, according to some uses, the withdrawal force should not exceed approximately 3.5 pounds.

It will be understood by those of skill in the art having the benefit of this disclosure that the drive spool 632 and gear train 634 configuration shown in FIG. 6 is exemplary in nature, and not limiting. Any gear configuration may be used to transmit a motive force generated by retraction of the suture 204 from the closure device 200 (FIG. 5) to provide an automatic driving force to the sealing plug 210 (FIG. 5) via the racks 644.

Figure 7:
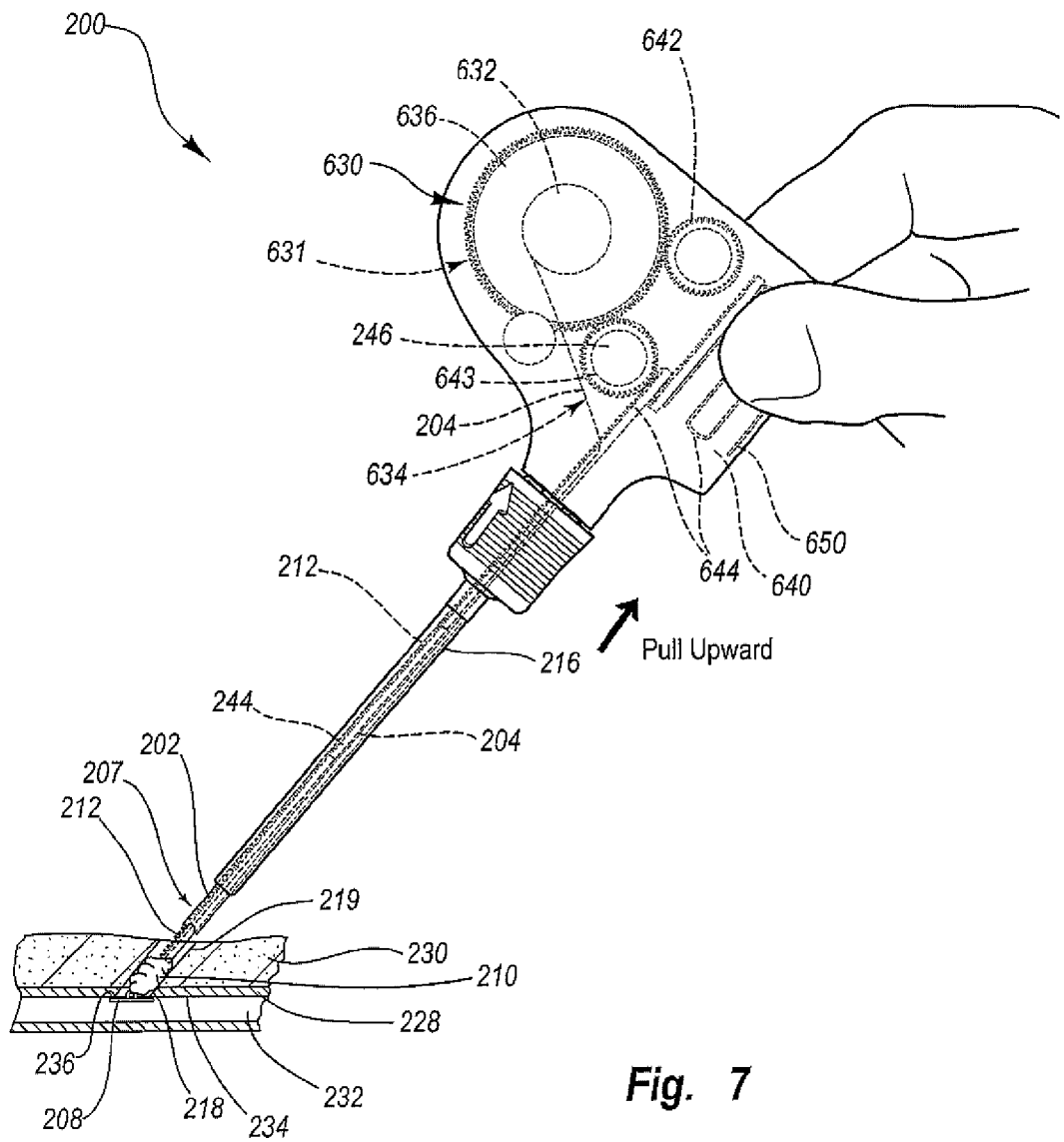
FIG. 7 is a side view of the closure device of FIG. 5 with the device being withdrawn and a sealing plug being automatically tamped according to one embodiment of the present invention.
Figure 7A:
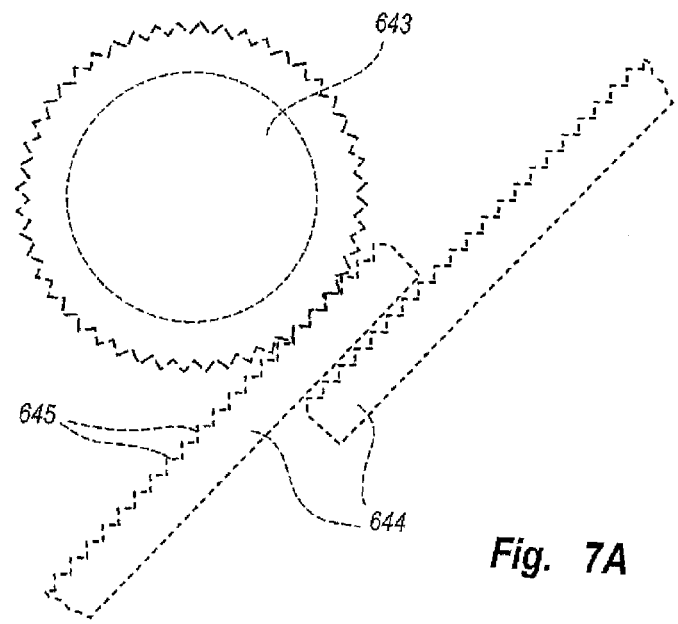
FIG. 7A is a close-up view of a portion of FIG. 7.

Accordingly, operation of the embodiment of FIGS. 5-7 is as follows. As the closing device 200 is retracted from a puncture tract as shown in FIG. 7, the suture 204, which is threaded through the anchor 208, unwinds from and causes rotation of the spool 632. The spool 632 drives the first gear 636 as it rotates via the coaxial connection between the spool 632 and the first gear 636. As the first gear 636 rotates, it drives the second gear 642. The second gear 642 drives one of the racks 644 in the magazine 640. The second gear 642 moves the racks 644 toward the third gear 643, which is also driven by the first gear 636. The third gear 643 drives the racks 644 distally, and the racks 644 drive the tamping tube 212. The tamping tube tamps the sealing plug 210 toward the anchor 208. Therefore, as the closing device 200 is retracted from the puncture tract 219, the sealing plug 210 is automatically tamped via the driving mechanism 630. The sealing plug 210 is more likely to create a sufficient arterial seal without gaps between the sealing plug 210 and the anchor 208, as may otherwise occur with a separate manual tamping procedure. Following tamping, the suture 204 may be cut and the anchor 208, the sealing plug 210, and the portion of the suture 204 extending therebetween remain, sealing the puncture 218. Moreover, the magazine 640 facilitates a compact device for tamping the sealing plug 210.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. An internal tissue puncture closure device, comprising:
   a filament extending from a first end of the closure device to a second end of the closure device;
   an anchor for insertion through a tissue wall puncture attached to the filament at the second end of the closure device;
   a sealing plug slidingly attached to the filament adjacent to the anchor;
   a driving mechanism for tamping the sealing plug toward the second end, the driving mechanism comprising a magazine housing a plurality of separate tamping devices;
   wherein the plurality of separate tamping devices each comprise a rack having a plurality of tines.

2. An internal tissue puncture closure device according to claim 1 wherein the magazine comprises a biasing member, and wherein the plurality of separate tamping devices are stacked in the magazine and biased in a first direction by the biasing member.

3. An internal tissue puncture closure device according to claim 1 wherein the driving mechanism comprises a transducer capable of effecting a distal force on one or more of the plurality of separate tamping devices upon withdrawal of at least a portion of the closure device from the tissue wall puncture.

4. An internal tissue puncture closure device according to claim 1 wherein the driving mechanism comprises:
   a transducer capable of effecting a distal force on one or more of the plurality of separate tamping devices upon withdrawal of at least a portion of the closure device from the tissue wall puncture, the transducer comprising:
      a first gear and spool assembly with a portion of the filament wound on the spool;
      wherein one or more of the plurality of tamping devices is directly or indirectly driven by the first gear.

5. An internal tissue puncture closure device according to claim 1 wherein the driving mechanism comprises:
   a transducer capable of effecting a distal force on one or more of the plurality of separate tamping devices upon withdrawal of at least a portion of the closure device from the tissue wall puncture, the transducer comprising:
      a first gear and spool assembly with a portion of the filament wound on the spool, the first gear and spool assembly disposed on a common axis and interconnected;
      a second gear meshed with the first gear;
      wherein one or more of the plurality of tamping devices is directly driven linearly by the second gear.

6. An internal tissue puncture closure device according to claim 1 wherein the driving mechanism comprises:
   a transducer capable of effecting a distal force on one or more of the plurality of separate tamping devices upon withdrawal of at least a portion of the closure device from the tissue wall puncture, the transducer comprising:
      a first gear and spool assembly with a portion of the filament wound on the spool, the first gear and spool assembly disposed on a common axis and interconnected;
      a second gear meshed with the first gear;
      a third gear meshed with the first gear;
      wherein one or more of the plurality of tamping devices is directly driven linearly by the second and third gears.

7. An internal tissue puncture closure device according to claim 1, further comprising a tamping tube slidingly disposed about the filament adjacent to the sealing plug;
   wherein the driving mechanism comprises:
      a transducer capable of effecting a distal force on one or more of the plurality of separate tamping devices upon withdrawal of at least a portion of the closure device from the tissue wall puncture, the transducer comprising:
         a first gear and spool assembly with a portion of the filament wound on the spool, the first gear and spool assembly disposed on a common axis and interconnected;
         a second gear meshed with the first gear;
         wherein one or more of the plurality of tamping devices is directly driven linearly by the second gear;
      wherein the one or more of the plurality of tamping devices abuts and drives the tamping tube and the sealing plug toward the anchor.

8. An internal tissue puncture closure device according to claim 1 wherein the driving mechanism comprises:
   a transducer capable of effecting a distal force on one or more of the plurality of separate tamping devices upon withdrawal of at least a portion of the closure device from the tissue wall puncture, the transducer comprising:
      a first gear and spool assembly with a portion of the filament wound on the spool, the first gear and spool assembly disposed on a common axis and interconnected;
      a magazine feed gear meshed with the first gear;
      a tamper gear meshed with the first gear;
      wherein one or more of the plurality of tamping devices is fed by the magazine feed gear to the tamper gear and driven by the tamper gear to tamp the sealing plug toward the anchor.

9. An internal tissue puncture closure device according to claim 1, further comprising a tamping tube disposed adjacent to the sealing plug;
   wherein the driving mechanism comprises an automatic driving mechanism;
   wherein the plurality of tamping devices is driven by the automatic driving mechanism in response to retraction of the closure devices;

wherein the tamping tube is driven by the plurality of tamping devices to tamp the sealing plug.

10. An internal tissue puncture closure device according to claim 1, further comprising a tamping tube disposed adjacent to the sealing plug;
  wherein the tamping tube is driven by the driving mechanism to tamp the scaling plug;
  wherein the driving mechanism comprises a transducer for effecting a tamping force on the sealing plug upon withdrawal of the closure device from the tissue wall puncture;
  wherein the transducer comprises:
  a first gear and spool assembly with a portion of the filament wound thereon;
  one or more of the plurality of tamping devices directly or indirectly driven by the first gear;
  wherein the spool rotates and drives the first gear in a first direction, and the first gear drives one or more of the plurality of tamping devices in a second direction, when the anchor is deployed and the closure device is retracted from the tissue wall puncture.

11. A tissue puncture closure device for partial insertion into and sealing of a tissue puncture in an internal tissue wall accessible through a percutaneous incision, comprising
  a handle portion;
  a carrier tube extending from the handle portion;
  a filament extending from the handle portion and through the carrier tube;
  a sealing plug disposed on the filament;
  a gear train housed in the handle portion;
  a spool operatively connected to the gear train;
  a portion of the filament wound on the spool;
  a magazine fed tamping device operatively connected to the gear train, the magazine fed tamping device comprising a plurality of separate tamping devices, wherein the plurality of separate tamping devices each comprise a rack having a plurality of tines.

12. A tissue puncture closure device for partial insertion into and sealing of a tissue puncture in an internal tissue wall accessible through a percutaneous incision according to claim 11 wherein the spool is coaxial with and connected to a gear of the gear train.

13. A tissue puncture closure device for partial insertion into and sealing of a tissue puncture in an internal tissue wall accessible through a percutaneous incision according to claim 11 wherein the magazine fed tamping device comprises a spring loaded set of stacked racks engagable with the gear train.

14. A tissue puncture closure device for partial insertion into and sealing of a tissue puncture in an internal tissue wall accessible through a percutaneous incision according to claim 11 wherein the gear train comprises a master gear and two slave gears each meshed with the master gear.

15. A tissue puncture closure device for partial insertion into and sealing of a tissue puncture in an internal tissue wall accessible through a percutaneous incision according to claim 11, further comprising an anchor attached to the filament at a distal end of the carrier tube, wherein the filament unwinds from the spool and drives the gear train in response to retraction of the handle portion from the tissue puncture if the anchor is deployed therein; wherein the gear train automatically drives the magazine fed tamping device; wherein the magazine fed tamping device tamps the sealing plug toward the anchor.

* * * * *